United States Patent [19]

Yamato

[11] Patent Number: 4,656,192
[45] Date of Patent: Apr. 7, 1987

[54] TROPOLONE DERIVATIVES, PROCESSES FOR THE PREPARATION THEREOF AND THE USE THEREOF AS ANTI-TUMOR AGENTS

[75] Inventor: Masatoshi Yamato, Okayama, Japan

[73] Assignee: Mect Corporation, Japan

[21] Appl. No.: 620,473

[22] Filed: Jun. 14, 1984

[51] Int. Cl.$^4$ .................. A61K 31/12; A61K 31/135; C07C 49/607; C07C 101/34

[52] U.S. Cl. ..................... 514/564; 514/567; 514/568; 514/569; 514/646; 514/648; 514/656; 514/657; 514/681; 514/682; 514/683; 514/680; 514/690; 514/691; 562/452; 562/473; 562/474; 564/305; 564/315; 564/330; 564/335; 568/326; 568/327; 568/328; 568/329; 568/325; 568/367; 568/375

[58] Field of Search ............... 549/347, 375; 568/326, 568/327, 328, 325, 329, 375, 367; 564/305, 315, 330, 335; 562/452, 473, 474; 514/568, 569, 567, 564, 646, 648, 656, 657, 690, 691, 683, 680, 681, 682

[56] References Cited

FOREIGN PATENT DOCUMENTS

| 286031 | 11/1953 | Japan | 568/347 |
| 37-11124 | 8/1962 | Japan | 568/347 |
| 41848 | 4/1979 | Japan. | |
| 61158 | 5/1979 | Japan. | |

OTHER PUBLICATIONS

Chem. Abstracts (1983), 99: 205726g.

*Primary Examiner*—Nicky Chan
*Attorney, Agent, or Firm*—Jacobs & Jacobs

[57] ABSTRACT

New tropolone derivatives of the general formula:

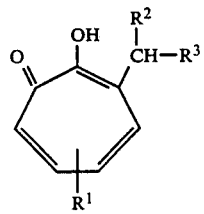

wherein $R^1$ represents H or an alkyl group, $R^2$ represents an alkyl, aryl, aralkyl or heterocyclic group and $R^3$ represents an alkoxyl, aryl or heterocyclic group or a group of the formula:

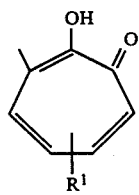

or $R^2$ and $R^3$ may form together a part of a heterocyclic group, their metal complex salts, processes for the preparation thereof and the use thereof as anti-tumor agents.

3 Claims, No Drawings

TROPOLONE DERIVATIVES, PROCESSES FOR THE PREPARATION THEREOF AND THE USE THEREOF AS ANTI-TUMOR AGENTS

BACKGROUND OF THE INVENTION

1. Field of the Invention

The present invention relates to new tropolone derivatives useful as anti-tumor agents and represented by the general formula (I):

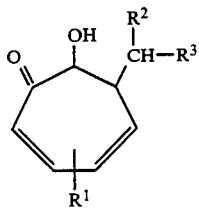

wherein $R^1$ represents H or an alkyl group, $R^2$ represents an alkyl, aryl, aralkyl or heterocyclic group and $R^3$ represents an alkoxyl, aryl or heterocyclic group or a group of the formula:

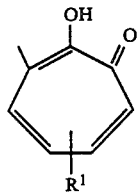

or $R^2$ and $R^3$ may form together a part of a heterocyclic group,
metal complex salts thereof,
and processes for the preparation thereof.

DESCRIPTION OF THE PRIOR ART

Among tropolone derivatives, some naturally occurring compounds and synthetic compounds have been studied on their pharmacological activities as anti-tumor agents. The results of these studies have been disclosed by, for example, Manfred Rösner et al., J. Med. Chem. (1981), 24, 257–261, Frank R. Quinn et al., ibid. (1981), 24, 251–256 and Arnold Brossi et al., ibid. (1983), 26, 1365–1369.

However, all of these tropolone derivatives are colchicine or its derivatives having chemical structures different from those of the tropolone derivatives of the present invention.

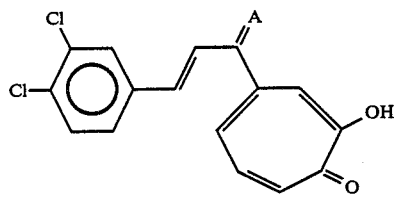

wherein A represents O or NOH
useful as starting materials for anti-tumor substances have been disclosed in the specification of Japanese Patent Public Disclosure No. 61156/1979.

4-[1-substituted-3-(3,4-dichlorophenyl)-2-propenyl]-tropolones useful as intermediates for anti-tumor agents have been disclosed in the specification of Japanese Patent Public Disclosure No. 61157/1979.

4-[1-acetamido-3-(3,4-dichlorophenyl)propyl]tropolone useful as a medicine such as an anti-tumor agent has been disclosed in the specification of Japanese Patent Public Disclosure No. 61158/1979.

Ester derivatives of tropolone useful as antimicrobial agents, hair growth stimulants and dental medicines have been disclosed in the specification of Japanese Patent Public Disclosure No. 41848/1979.

However, the tropolone derivatives of the present invention are new compounds having pharmacological effects useful as anti-tumor agents and have not been disclosed in any of the above-mentioned literature or specifications.

SUMMARY OF THE INVENTION

The present invention provides tropolone derivatives of the general formula:

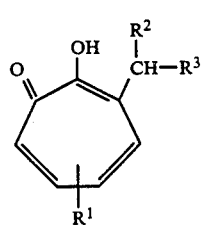

wherein $R^1$ represents H or an alkyl group, $R^2$ represents an alkyl, aryl, aralkyl or heterocyclic group and $R^3$ represents an alkoxyl, aryl or heterocyclic group or a group of the formula:

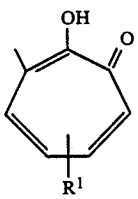

or $R^2$ and $R^3$ may form together a part of a heterocyclic group,
and metal complex salts thereof.

Further, the present invention provides a process for preparing tropolone derivatives of the general formula:

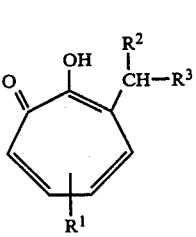

wherein $R^1$ represents H or an alkyl group, $R^2$ represents an alkyl, aryl or aralkyl group and $R^3$ represents an alkoxyl group or a group of the formula:

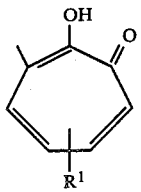

characterized by reacting a compound of the formula:

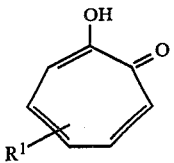
(II)

wherein $R^1$ has the same meaning as above with a compound of the formula:

$$R^2-CH(OR^{3'})_2 \quad (III)$$

wherein $R^2$ has the same meaning as above and $R^{3'}$ represents an alkyl group.

The present invention provides also a process for preparing tropolone derivatives of the general formula:

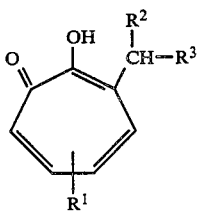

wherein $R^1$ represents H or an alkyl group, $R^2$ represents an alkyl, aryl or aralkyl group and $R^3$ represents an aryl or a heterocyclic group characterized by reacting a compound of the formula:

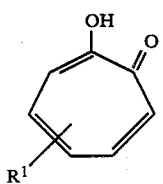
(II)

wherein $R^1$ has the same meaning as above with a compound of the formua:

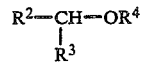

wherein $R^2$ and $R^3$ have the same meaning as above and $R^4$ represents an alkyl, aryl or aralkyl group.

The present invention provides also an anti-tumor agent characterized by containing as an active ingredient a tropolone derivative of the general formula:

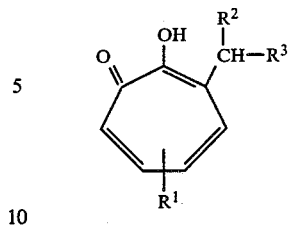
(I)

wherein $R^1$ represents H or an alkyl group, $R^2$ represents an alkyl, aryl, aralkyl or heterocyclic group and $R^3$ represents an alkoxyl, aryl or heterocyclic group or a group of the formula:

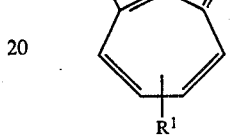

or $R^2$ and $R^3$ may form together a part of a heterocyclic group,
and a metal complex salt thereof.

DETAILED DESCRIPTION OF THE PREFERRED EMBODIMENTS

The present invention relates to new tropolone derivatives and metal complex salts thereof useful as antitumor agents, process for the preparation thereof and the use of these compounds.

The tropolone derivatives are represented by the following general formula I:

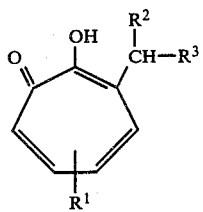
(I)

wherein $R^1$ represents H or an alkyl group, $R^2$ represents an alkyl, aryl, aralkyl or heterocyclic group and $R^3$ represents an alkoxyl, aryl or heterocyclic group or a group of the formula:

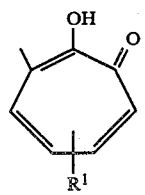

or $R^2$ and $R^3$ may form together a part of a heterocyclic group.

Explanation of $R^1$ $R^1$ represents H or an alkyl group. The term "alkyl group" herein indicates a straight chain or branched alkyl group having about 1 to 5 carbon atoms such as methyl, ethyl or n- or iso-propyl group.

Explanation of $R^2$ $R^2$ represents an alkyl, aryl, aralkyl or heterocyclic group.

The alkyl groups are saturated or unsaturated alkyl groups having about 3 to 5 carbon atoms.

The aryl groups are substituted or unsubstituted aryl groups having about 6 to 20 carbon atoms. The aryl groups include, for example, phenyl, naphthyl, anthryl and indenyl groups. The substituents include, for example, hydroxy group, alkoxyl groups such as methoxyl, ethoxyl and n- or iso-propoxyl groups, the above-mentioned alkyl groups, halogens, as well as dimethylamino, diethylamino and carboxyl groups.

The aralkyl groups are those having about 7 to 20 carbon atoms such as benzyl, phenethyl, styryl and benzhydryl groups.

The heterocyclic groups are those having 5 to 7 members. The hetero atoms are oxygen, nitrogen and sulfur. The heterocyclic groups include, for example, the following groups:

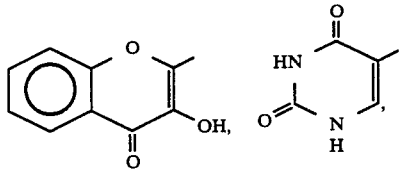

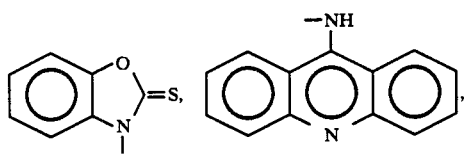

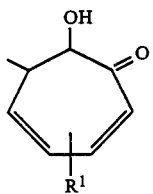

Explanation of $R^3$ $R^3$ represents an alkoxyl, aryl or heterocyclic group or a group of the formula:

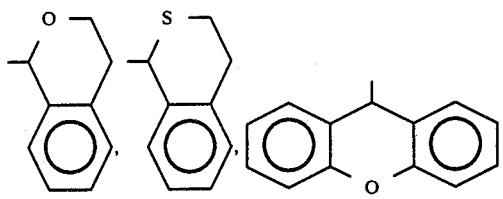

The alkoxyl groups are those having about 1 to 8 carbon atoms. The alkoxyl groups include, for example, those listed above as the substituents of the aryl groups and aralkyloxy groups such as benzyloxy group.

The aryl groups and the heterocyclic groups are those shown with reference to $R^2$.

In the present invention, the groups $R^2$ and $R^3$ may form together a part of a heterocyclic group. In such a case, for example, the following heterocyclic groups are formed from $R^2$, $R^3$ and —CH<:

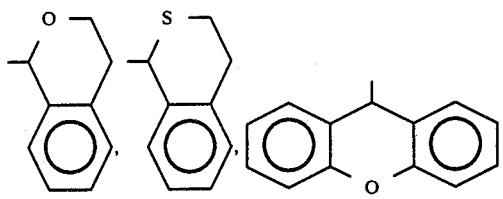

Now, the description will be made on processes for the preparation of the tropolone derivatives of the present invention.

(A) Preparation process (1)

This process may be shown by the following chemical formulae:

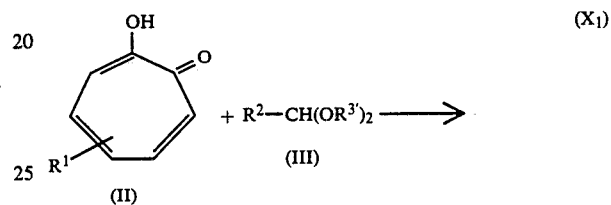

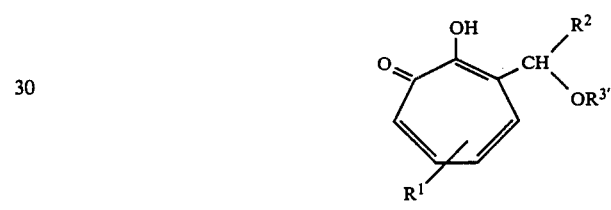

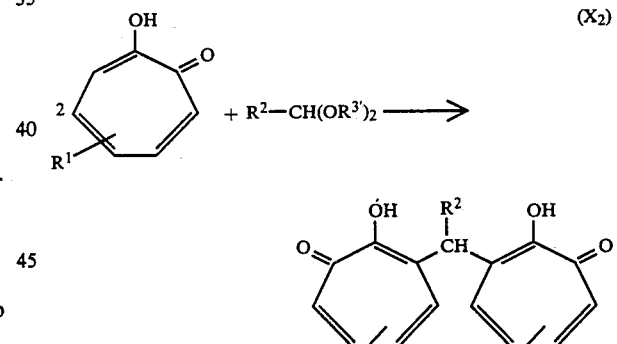

In the formula (III), $R^{3'}$ represents an alkyl or aralkyl group.

The tropolone compound of the formula (II) is reacted with the acetal compound of the formula (III) as shown above to form the tropolone derivative of the present invention.

A typical example of the tropolone compounds of the formula (II) is 4-isopropyltropolone (i.e. hinokitiol) which is easily available on the market.

The acetal compound of the formula (III) includes, for example, benzaldehyde dimethylacetal, benzaldehyde diethylacetal, acetaldehyde dimethylacetal, acetaldehyde diethylacetal, cinnamaldehyde diethylacetal and crotonaldehyde diethylacetal.

The above-mentioned reactions ($X_1$) and ($X_2$) are carried out in an inert atmosphere of argon or nitrogen, for example, at a temperature of about 160 to 180° C. for about 2 to 10 h. These reactions are carried out generally under atmospheric pressure. However, when an acetal having a low boiling point is used, it is desirable to effect the reaction under an elevated pressure. These reactions are carried out preferably in the absence of any solvent but if necessary, a suitable solvent may be used. As the solvent, there may be used xylene, tetralin, quinoline, or the like.

In the reaction ($X_1$), the acetal compound of the formula (III) is used in an amount of about 1 to 2 moles per mol of the compound of the formula (II).

In the reaction ($X_2$), the acetal compound of the formula (III) is used in an amount of about one-half of that used in the reaction ($X_1$).

The reaction product may be purified by an ordinary method. For example, a poor solvent such as petroleum ether is added to the reaction product, crystals thus formed are filtered out, and the filtrate is treated by column chromatography. After elution followed by precipitation of crystals, the crystals thus obtained are combined together and recrystallized from a suitable solvent.

When the intended product is in liquid form, the reaction product may be purified by, for example, subjecting the same to column chromatography, if necessary, and then distilling the product.

(B) Preparation process (2)

This process may be shown by the following chemical formulae:

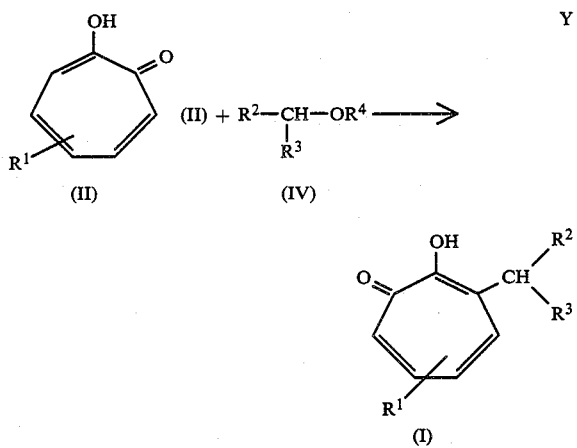

In the formula (IV), $R^4$ represents an alkyl, aralkyl or aryl group and $R^3$ does not represent an alkoxyl group.

The acetal compounds or ethers of the formula (IV) include, for example, 1-ethoxyisochroman, ethyl benzhydryl ether,

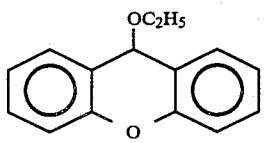

and ethyl 9-phenoxathiinyl ether.

The reaction (Y) may be carried out under substantially the same conditions as in the above process (1). Namely, the reaction is carried out in an inert atmosphere at a temperature of about 160° to 180° C. under atmospheric pressure or, if necessary, under an elevated pressure for about 10 to 20 h. This reaction is carried out preferably in the absence of any solvent but, if necessary. the above-mentioned solvent may be used.

The acetal compound or ether of the formula (IV) is used in an amount of about 1 to 2 mols per mol of the tropolone compound of the formula (II).

The thus obtained reaction product is purified in the same manner as above.

(C) Process for the preparation of the metal complex salts of the tropolone derivatives of the invention The metal complex salts may be prepared by an ordinary process.

For example, the tropolone derivative obtained as described above is dissolved in a suitable solvent, then an aqueous solution of a metal salt of an inorganic or organic acid is suspended therein, the suspension is stirred for about 1 to 2 h and the solvent is separated from aqueous layer and concentrated to dryness to obtain the metal complex salt.

The solvents usable in this reaction include, for example, chloroform and ether. The metal salts are, for example, copper, iron, magnesium and calcium salts of inorganic acids such as hydrochloric acid, sulfuric acid and nitric acid and organic acids such as acetic acid, tartaric acid and citric acid.

It has been found that the thus obtained tropolone derivatives and metal complex salts thereof of the present invention have strong anti-tumor effects and they are usable as medicines.

The pharmacological activities of the compounds were determined by animal tests with a dosage of 1 to 500mg/kg. In the treatment of human beings, the dosage is, for example, 0.1 to 25 mg/kg. As a matter of course, doses outside this range may be used at the discretion of the physician treating the patient.

The compounds of the present invention have only a low acute toxicity. For example, the acute toxicities of typical compounds, i.e., α,α-bis(2-hydroxy-6-isopropyl-tropon-3-yl)toluene (IIIa) and α,α-bis(2-hydroxy-6-isopropyl-tropon-3-yl)-4-methoxytoluene (IIIb) have $LD_{50}$ as shown in the following table:

| Acute toxicity of IIIa in mice | | |
|---|---|---|
| Route | Sex | $LD_{50}$ (mg/kg) |
| p.o. | Male | >5,000 |
| i.p. | Male | 5.5 |
| i.v. | Male | 5.8 |

| Acute toxicity of IIIb in mice | | |
|---|---|---|
| Route | Sex | $LD_{50}$ (mg/kg) |
| p.o. | Male | >5,000 |
| i.p. | Male | 11.2 |
| i.v. | Male | 9.1 |

When a human being is treated with the compounds of formula I, the dose thereof is for example, between 0.1 and 25 mg/kg. but, of course, doses outside this range may be used at the discretion of the physician treating the patient. The pharmacologically active compounds of formula I may be administered by the enteral or parenteral routes and for this purpose they will normally be formulated into pharmaceutical compositions comprising the active ingredient in association with at least one pharmaceutically acceptable carrier therefor.

Such compositions form a part of this invention and will normally consist of the active ingredient mixed with a carrier, or diluted by a carrier, or enclosed or encapsulated by a carrier in the form of a capsule, sachet, cachet or other container. The carrier may be a solid, semi-solid or liquid material which serves as a vehicle, excipient, coating agent, or medium for the active ingredient. Some examples of the carriers which may be used are lactose, dextrose, sucrose, sorbitol, mannitol, starch, gum acacia, calcium phosphate, liquid paraffin, cocoa butter, oil of theobroma, alginates, tragacanth, gelatin, methyl cellulose, polyoxyethylene sorbitan monolaurate, methyl- or propyl-hydroxybenzoate, ethyl cellulose acetate phthalate, low viscosity acetyl cellulose acetate, paraffin wax, mineral wax, vegetable wax, vegetable gum, silicone rubbers such as liquid polydimethylsiloxane rubber, plasticised or unplasticised polyvinyl chloride, plasticised polyethylene terephthalate, modified collagen, cross-linked hydrophilic polyether gel, cross-linked polyvinyl alcohol or cross-linked partially hydrolysed polyvinyl acetate.

Advantageously the compositions of the invention are formulated in a dosage unit form containing from 1 to 1000 mg (preferably 25 to 500 mg) of the active ingredient. Examples of suitable dosage unit forms are tablets, hard or soft gelatin capsules, microcapsules and suppositories as well as drug dispensing systems comprising the active ingredient contained in a flexible, imperforate polymeric material through which the drug may be released slowly by diffusion. More generally, the term "dosage unit form" as used herein means a physically discrete unit containing the active ingredient, generally in admixture with and/or enclosed by a pharmaceutical carrier, the quantity of active ingredient being such that one or more units are normally required for a single therapeutic administration.

In addition to the active ingredient of formula I, the compositions of the present invention may also contain one or more pharmacologically active ingredients, for example, acetylsalicyclic acid and salts thereof, caffeine, codeine phosphate, phenylbutazone, paracetamol, dextropropoxyphene and indomethacin.

The compositions of the present invention will of course be adapted to the particular route of administration. Thus, for oral administration, tablets, pills, capsules, solutions or suspensions may be used, for parenteral administration, sterile injection solutions or suspensions may be used; for rectal administration, suppositories may be used; and for topical administration, creams, lotions or ointments may be used. Any of the foregoing compositions may, of course, be formulated in delayed or sustained release form in a manner well known in the art.

The present invention will be further illustrated by the following examples, which by no means limit the invention.

EXAMPLE 1

Preparation of
3-(o-ethoxybenzyl)-6-isopropyltropolone (Ia)
(compound of the above formula wherein $R^1$ is isopropyl, $R^2$ is phenyl and $R^3$ is ethyl group)

A mixture of benzaldehyde diethylacetal (7.3 g, 40 mmol) and hinokitiol (3.2 g, 20 mmol) was stirred under heating to 150° C. in argon gas stream for 12 h. The reaction mixture was treated according to silica gel column chromatography to obtain a viscous liquid. This liquid was subjected to a fractional distillation to obtain a fraction of b.p. 130 to 140° C./0.005 mmHg, whereby 1.3 g (22 %) of Ia was obtained. NMR (CDCl$_3$)δ: 1.24 (6H, d, J=7 Hz), 1.25 (3H, t, J=7 Hz), 2.85 (1H, m), 3.58 (2H, q, J=7 Hz), 6.12 (1H, s), 6.93–7.68 (7H, m), 7.95 (1H, d, J=10 Hz), 9.26 (1H, broad). MS: m/e: 298(M+). Anal. Calcd C$_{19}$H$_{22}$O$_3$: C, 76.48; H, 7.43, Found: C, 76.52; H, 7.48.

EXAMPLE 2

Preparation of 3-(α-ethoxy-4-methylbenzyl)-6-isopropyltropolone (Ib) (compound of the above formula wherein $R^1$ is isopropyl, $R^2$ is 4-methylphenyl and $R^3$ is ethyl group)

A mixture of 4-methylbenzaldehyde diethyl acetal (6.4 g, 33 mmol) and hinokitiol (2.8 g, 17 mmol) was stirred under heating to 150° C. in argon gas stream for 6 h. The reaction mixture was treated by silica gel column chromatography to obtain 1.3 g (25 %) of Ib (b.p. 160 to 170° C./0.005 mmHg) in the form of a viscous liquid. NMR (CDCl$_3$)δ: 1.20 (3H, t, J=7 Hz), 1.38 (6H, d, J=7 Hz), 2.29 (3H, s), 2.60–3.20 (1H, m), 3.51 (2H, q, J=7 Hz), 5.97 (1H, s), 6.70–8.00 (7H, broad), 8.70–9.30 (1H, broad). MS m/e: 312 (M+). Anal. Calcd C$_{20}$H$_{24}$O$_3$: C, 76.89; H, 7.74, Found: C, 76.87, H, 7.80.

EXAMPLE 3

Preparation of
3-(α-ethoxy-4-methoxybenzyl)-6-isopropyltropolone
(Ic) (compound of the above formula wherein $R^1$ is isopropyl, $R^2$ is 4-methoxyphenyl and $R^3$ is ethyl group)

A mixture of 4-methoxybenzaldehyde diethylacetal (5.5 g, 26 mmol) and hinokitiol (4 g, 24 mmol) was heated to 150° C. in argon gas stream for 10 h. The reaction mixture was treated according to silica gel column chromatography to obtain 1.5 g (18.5 %) of a viscous liquid. bp 180° C./0.005 mmHg. NMR (CDCl$_3$)δ: 1.30 (6H, d, J=7 Hz), 1.30 (3H, t, J=7 Hz), 2.85 (1H, m), 3.58 (2H, q, J=7 Hz), 3.80 (3H, s), 6.08 (1H, s), 6.70–7.60 (7H, m), 8.05 (1H, d, J=10 Hz). MS m/e: 328(M+). Anal. Calcd C$_{20}$H$_{24}$O$_4$: C, 73.14; H, 7.37. Found: C, 73.32; H, 7.50.

EXAMPLE 4

Preparation of
3-(1-isochromanyl)-6-isopropyltropolone (IIa)
(compound of the above formula wherein $R^1$ is isopropyl group)

A mixture of 1-ethoxyisochroman (8 g, 45 mmol) and hinokitiol (5 g, 30 mmol) was heated to 150° to 160° C. in argon gas stream for 6 h. The reaction mixture was treated by silica gel column chromatography to obtain 5.9 g (66 %) of crystals (IIa) having m.p. of 135° to 138° C. NMR (CDCl$_3$)δ: 1.23 (6H, d, J=7 Hz), 2.50–3.50 (3H, m), 3.80–4.45 (2H, m), 6.62 (1H, s), 6.72–7.40 (7H, m), 7.50 (1H, d, j=10 Hz), 9.30 (1H, broad). MS m/e: 296(M+). Anal. Calcd C$_{19}$H$_{20}$O$_3$: C, 77.00; H, 6.80. Found: C, 77.23; H, 6.92.

EXAMPLE 5

Preparation of 3-(1-isochromanyl)tropolone (IIb)
(compound of the above formula wherein $R^1$ is H)

A mixture of 1-ethoxyisochroman (2.9 g, 16 mmol) and tropolone (1.3 g, 10 mmol) was heated to 150° to 160° C. in an argon gas stream for 16 h. The reaction mixture was treated by silica gel column chromatography to obtain 1.3 g (46 %) of IIb. mp 175–178° C. NMR (CDCl$_3$)δ: 2.53–3.51 (2H, m), 3.80–4.54 (2H, m), 6.65

(1H, s), 6.73–7.71 (7H, m), 9.03–9.65 (1H, broad), MS m/e: 254(M+). Anal. Calcd $C_{16}H_{14}O_3$: C, 75.57; H, 5.55. Found: C, 75.61; H, 5 51.

EXAMPLE 6

Preparation of 3-[α-ethoxy-4-(N,N-dimethylamino)benzyl]-6-isopropyltropolone (Id) (compound of the above formula wherein $R^1$ is isopropyl and $R^2$ is N,N-dimethylaminophenyl group)

A mixture of hinokitiol (4 g, 24 mmol) and N,N-dimethylaminobenzaldehyde diethylacetal (6.53 g, 29 mmol) was heated to 150° C. in argon gas stream for 7 h. The reaction mixture was treated by silica gel column chromatography using petroleum ether/ethyl acetate (12/1). After a recrystallization from petroleum ether, 0.88 g (10.6 %) of crystals (Id) were obtained. mp 72° C. NMR (CDCl$_3$)δ: 1.20 (6H, d, J=7 Hz), 1.30 (3H, t, J=7 Hz), 2.50–3.00 (1H, m), 2.81 (6H, s), 3.55 (2H, q,.J=7 Hz), 6.01 (1H, s), 6.50–8.20 (7H, m), 9.21 (1H, b). MS m/e: 341(M+). Anal. Calcd $C_{21}H_{27}NO_3$: C, 73.83; H, 7.97; N, 4.10. Found: C, 74.07; H, 7.95; N, 4.12.

EXAMPLE 7

Preparation of 3-benzhydryl-6-isopropyltropolone (Ie) (compound of the above formula wherein $R^1$ is isopropyl group and $R^2$ and $R^3$ are phenyl group)

A mixture of ethyl benzhydryl ether (8 g, 37 mmol) and hinokitiol (6.2 g, 37 mmol) was heated to 180° C. in argon gas stream for 20 h. The reaction mixture was treated by silica gel column chromatography to obtain crystals having m.p. of 146° to 147° C. Yield: 1.2 g (8 %). NMR (CDCl$_3$)δ: 1.24 (6H, d, J=7 Hz), 2.85 (1H, m), 6.34 (1H, s), 7.0–7.4 (13H, m), 9.15–9.65 (1H, broad). MS m/e: 330 (M+). Anal. Calcd $C_{23}H_{22}O_2$: C, 83.60; H, 6.71. Found: C, 83.75; H, 6.80.

EXAMPLE 8

Preparation of 3-benzyl-6-isopropyltropolone (If) (compound of the above formula wherein $R^1$ is isopropyl, $R^2$ is hydrogen and $R^3$ is phenyl group)

A mixture of benzyl alcohol (4.6 g, 43 mmol), dicyclohexylcarbodiimide (DCC) (8.8 g, 43 mmol) and a catalytic amount of cuprous chloride was heated to 50° to 60° C. for 24 h. Hinokitiol (7 g, 43 mmol) was added to the mixture and they were heated to 100° C. for 3 h. The resulting mixture was dissolved in ethyl acetate. C.rystals thus formed were filtered out. The filtrate was concentrated and the resulting residue was purified according to a silica gel column chromatography. After the elution with petroleum ether/ethyl acetate (20:1), a mixture of 2-benzyloxy-4-isopropyltropone and 7-benzyloxy-3-isopropyltropone was obtained in the form of a viscous liquid.

The mixture was dissolved in decalin (50 ml). The solution was heated to 190° C. for 12 h. The solvent was distilled off under reduced pressure and the resulting residue was purified by silica gel column chromatography. After elution with petroleum ether/ethyl acetate (20:1) followed by recrystallization from methanol, 0.6 g (5 %) of If was obtained. mp 63°–65° C. NMR (CDCl$_3$)δ: 1.25 (6H, d, J=7 Hz), 2.55–3.40 (1H, m), 4.16 (2H, s), 6.80–7.50 (4H, m), 7.32 (5H, s).

EXAMPLE 9

Preparation of α,α-bis(2-hydroxy-6-isopropyl-tropon-3-yl)toluene (IIIa) (compound of the above formula wherein $R^1$ is isopropyl and $R^2$ is phenyl group)

A mixture of hinokitiol (3.2 g, 20 mmol) and benzaldehyde diethylacetal (2.9 g, 16 mmol) was heated to 180° C. in argon gas stream for 12 h. After completion of the reaction, petroleum ether was added to the reaction mixture and then crystals thus formed were filtered out. The mother liquor was treated according to a silica gel (petroleum ether/ethyl acetate: 10/1) column chromatography to form crystals. The crystals were combined and recrystallized from methanol to obtain 1.5 g (34 %) of crystals(IIIa) mp 199°–200° C. NMR (CDCl$_3$)δ: 1.27 (12H, d, J=7 Hz), 2.48–3.26 (2H, m), 6.76 (1H, s), 6.82–7.44 (10H, m), 9.53 (2H, broad), MS m/e: 416 (M+) Anal. Calcd $C_{27}H_{28}O_4$: C, 77.86; H, 6.78. Found: C, 77.79; H, 6.82

EXAMPLE 10

Preparation of α,α-bis(2-hydroxy-6-isopropyl-tropon-3-yl)-4-methoxytoluene (IIIb) (compound of the above formula wherein $R^1$ is isopropyl and $R^2$ is 4-methoxypenyl qroup)

A mixture of hinokitiol (4 g, 24 mmol) and anisaldehyde diethylacetal (2.5 g, 12 mmol) was heated to 180° C. in argon gas stream for 2 h. After completion of the reaction, the mixture was dissolved in hot methanol. The solution was cooled to form crystals. The crystals were filtered out and the mother liquor was concentrated and then treated by silica gel column chromatography to form crystals. The crystals were combined together and recrystallized from ethanol to obtain crystals (IIIb) having m.p. of 204° to 205° C. Yield: 1.8 g (33.6 %). NMR (CDCl$_3$)δ: 1.30 (12H, d, J=7 Hz), 2.48–3.24 (2H, m), 3.85 (3H, s), 6.56 (1H, s), 6.60–7.51 (10H, m), 9.02 (2H, broad). MS m/e: 446 (M+). Anal. Calcd $C_{28}H_{30}O_5$ C., 75.31; H, 6.77. Found: C,75.42; H, 6.75.

EXAMPLE 11

Preparation of α,α-bis(2-hydroxy-6-isopropyl-tropon-3-yl)-4-methyltoluene (IIIc) (compound of the above formula wherein $R^1$ is isopropyl and $R^2$ is 4-methylphenyl qroup)

A mixture of hinokitiol (3.28 g, 20 mmol) and 4-methylbenzaldehyde diethylacetal (2.4 g, 12 mmol) was heated to 180° C. in argon gas stream for 6 h. Petroleum ether was added to the reaction liquid and crystals thus formed were filtered out. The mother liquor was treated by silica gel column chromatography. Crystals were obtained from a fraction eluted with a solvent mixture of petroleum ether and ethyl acetate. The crystals were combined and recrystallized from benzene to obtain 1.60 g (37.2 %) of crystals having m.p. of 231° to 233° C. NMR (CDCl$_3$)δ: 1.28 (12H, d, J=6 Hz), 2.37 (3H, s), 2.50–3.30 (2H, m), 6.65 (1H, s), 6.70–7.50 (10H, broad), 9.00–9.72 (2H, broad). MS m/e: 430 (M+). Anal. Calcd $C_{28}H_{30}O_4$ C, 78.10; H, 7.04. Found: C, 78.19; H, 7.11.

EXAMPLE 12

Preparation of
α,α-bis(2-hydroxy-6-isopropyl-tropon-3yl)-4-chlorotoluene (IIId) (compound of the above formula wherein $R^1$ is isopropyl and $R^2$ is 4-chlorophenyl group)

A mixture of hinokitiol (3.28 g, 20 mmol) and 4-chlorobenzaldehyde diethyl acetal (2.57 g, 12 mmol) was heated to 180° C. in argon gas stream for 6 h. Petroleum ether was added to the reaction mixture and crystals thus formed were filtered out. The mother liquor was treated by silica gel column chromatography. By elution with a solvent mixture of petroleum ether/ethyl acetate (32/1), crystals were formed. The crystals were combined and recrystallized from benzene to obtain crystals having m.p. of 227° to 228° C. Yield: 1.6 g (35 %). NMR (CDCl$_3$)δ: 1.14 (12H, d, J=8 Hz), 2.35-3.15 (2H, m), 6.62 (1H, s), 6.67-7.55 (10H, broad), 9.05-9.70 (2H, broad). MS m/e: 451 (M+). Anal. Calcd C$_{27}$H$_{27}$O$_4$Cl: C, 71.90; H, 6.05. Found: C, 71.66; H, 5.98.

EXAMPLE 13

Preparation of
α,α-bis(2-hydroxy-6-isopropyl-tropon-3-yl)-4-methoxytoluene/copper complex salt (IIIb-Cu) (compound of the above formula wherein $R^1$ is isopropyl and $R^2$ is 4-methoxyphenyl group)

IIIb (0.5 g, 1.12 mmol) obtained in Example 10 was dissolved in 30 ml of chloroform. A suspension of copper acetate (0.5 g, 2.2 mmol) in a small amount of water was added to the solution and the mixture was stirred for 2 h. A chloroform layer was taken out, washed with water and dryed. The solvent was concentrated to obtain 0.49 g (85 %) of green crystals having m.p. of at least 300° C. Anal. Calcd C$_{28}$H$_{28}$O$_5$Cu: C, 70.29; H, 5.83. Found: C, 70.41; H, 5.91.

EXAMPLE 14

Preparation of
α,α-bis(2-hydroxy-6-isopropyl-tropon-3-yl)-4-(N,N-dimethylamino)toluene (IIIe) (compound of the above formula wherein $R^1$ is isopropyl and $R^2$ is 4-N,N-dimethylaminophenyl group)

N,N-dimethylaminobenzaldehyde diethylacetal (1.36 g, 6 mmol) was added to hinokitiol (2 g, 12 mmol). The mixture was heated to 180° C. in argon gas stream for 2 h. After completion of the reaction, the product was treated by silica gel column chromatography. By elution with petroleum ether/ethyl acetate (12/1), crystals were obtained. After recrystallization from petroleum ether/ethyl acetate (12/1), 0.86 g (30.7 %) of crystals (Ie) (IIIe) were obtained. m.p. 224°-226° C. NMR CDCl$_3$δ: 1.32 (12H, d, J=7 Hz), 2.98 (6H, s), 2.70-3.20 (2H, m), 6.62 (1H, s), 6.70-7.60 (10H, m), 8.00-9.20 (2H, b). MS m/e: 459 (M+) Anal Calcd C$_{29}$H$_{33}$NO$_4$: C, 75.79; H, 7.24; N, 3.05. Found: C, 75.58; H, 7.25; N, 2.93.

EXAMPLE 15

Preparation of
α,α-bis(2-hydroxy-5-isopropyltropon-3-yl)-4-methoxytoluene (IVa)

4.9 g (30 mmol) of γ-thujaplicin and 3.5 g (17 mmol) of anisaldehyde diethylacetal charged in a flask were stirred under heating to 180° C. for 2 h while the gas in the flask was replaced with argon. The reaction mixture was treated by silica gel column chromatography and then eluted with petroleum ether/ethyl acetate (10/1).

The resulting crystalline fraction was recrystallized from methanol/CH$_2$Cl$_2$ to obtain 0.7 g (13 %) of α,α-bis(2-hydroxy-5-isopropyl-tropon-3-yl)-4-methoxytoluene (IVa). NMR (CDCl$_3$)δ: 1.25 (12H, d, J=7 Hz, CH(Me)$_2$x2), 2.58-3.18 (2H, m, CH(Me)$_2$x2), 3.76 (3H, s, OCH$_3$), 6.65 (1H, s, CH), 6.68-7.58 (10H, m, tropolone H and aromatic H); MS m/e: 446 (M+). Anal Calcd. C$_{28}$H$_{30}$O$_5$: C, 75.31; H, 6.97. Found: C, 75.49; H, 7.01.

EXAMPLE 16

Anti-tumor tests

KB-cell growth inhibition tests:

KB-cells were placed in an Eagles minimal essential medium (MEM)-10% calf serum medium and cultered in a 5 % carbon dioxide atmosphere at 37° C. in an incubator. The cells thus treated were used in the tests. On the first day, the KB cells were diluted to a concentration of 2×10$^4$/ml 3 ml of the resulting suspension was placed in watch glasses having a diameter of 60 mm. On the second day, 100, 30, 10, 3 and 1 μg/ml of each sample to be tested was added thereto and the culture was continued under the same conditions as above. On the fourth day, the surviving cells were taken out of the watch glass by meand of trypsin and the number of the cells was counted. The concentration of the sample required for obtaining substantially 50 % growth inhibition based on the sample-free control (ED$_{50}$) was determined. The cancer cell growth inhibition effect of the sample was shown by ED$_{50}$. The results are shown in Table 1.

Tests of life-prolongation effects on cancered mice:

10$^6$ P388 cancer cells were grafted into groups of CDF mice. Each group consisted of six mice. On the first day and the fifth day, a sample to be tested was administered to the mice intraperitoneally. The life-prolongation effects were shown in terms of the ratio of the number of surviving days of the mice in the treated group to that in the control group (T/C %). The results are shown in Tables 1 and 2.

TABLE 1

Results of anti-tumor tests:

| Compound | $R^1$ | Substituent $-CH<^{R^2}_{R^3}$ | | KB cell growth inhibition ED$_{50}$ (μg/ml) | life-prolongation effects T/C % (mg/kg) |
|---|---|---|---|---|---|
| Ia | —CH(CH$_3$)$_2$ | 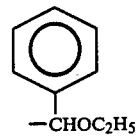 | | <0.3 | 109(200) |
| Ib | " | CH$_3$ 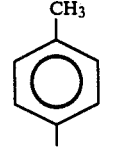 —CHOC$_2$H$_3$ | | 6.2 | 125(400) |

TABLE 1-continued

Results of anti-tumor tests:

| Compound | R¹ | Substituent $-CH\begin{smallmatrix}R^2\\R^3\end{smallmatrix}$ R² / R³ | KB cell growth inhibition ED$_{50}$ (μg/ml) | life-prolongation effects T/C % (mg/kg) |
|---|---|---|---|---|
| Ic | " | OCH₃ on phenyl; —CHOC₂H₅ | 0.51 | 140(100) |
| Id | " | H₃C—N—CH₃ on phenyl; —CHOC₂H₅ | 0.59 | 136(100) |
| Ie | " | —CH(phenyl)(phenyl) | 1.39 | 132(400) 123(200) |
| If | " | —CH(H)(phenyl) | 0.56 | 97(200) |
| IIa | " | 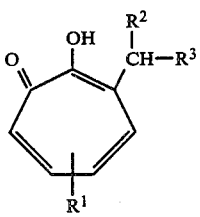 | <0.3 | 126(100) |
| IIb | H | (isochroman group) | 2.23 / 0.5 | 96(100) 104(100) |

TABLE 2

Results of anti-tumor tests

| Compound | Substituents¹ R¹ | R² | KB cell growth inhibition ED$_{50}$ (μg/ml) | Life-prolongation effects T/C % (mg/kg) |
|---|---|---|---|---|
| IIIa | —CH(CH₃)₂ | —phenyl | <0.3 | 188(5) 132(1.25) |
| IIIb | " | —C₆H₄—OCH₃ | <0.3 | 173(5) 127(0.62) |
| IIIc | " | —C₆H₄—CH₃ | 1.45 | 163(10) 125(2.5) |
| IIId | " | —C₆H₄—Cl | 2.0 | 144(10) 124(2.5) |
| IIIe | " | —C₆H₄—N(CH₃)₂ | 0.69 | 141(2.5) |
| IVa | "² | —C₆H₄—OCH₃ | 0.3 | 147(10) 137(2.5) |

Notes:
¹R³ has the following formula:

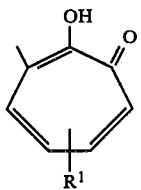

²Isopropyl group as R¹ is in 5-position.

What is claimed is:

1. A tropolone derivative of the general formula:

$$\text{(I)}$$

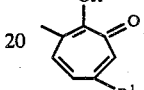

wherein
R¹ represents hydrogen or alkyl of 1 to 5 carbon atoms;
R² represents alkyl of 3 to 5 carbon atoms; aryl of 6 to 20 carbon atoms, unsubstituted or substituted by a substituent selected from the group consisting of hydroxy, alkoxy of 1 to 8 carbon atoms, alkyl of 1 to 5 carbon atoms, halogen, dimethylamino, diethylamino and carboxyl; aralkyl of 7 to 20 carbon atoms; and
R³ represents alkoxy of 1 to 8 carbon atoms; aryl of 6 to 20 carbon atoms, unsubstituted or substituted by a said substituent; or (tropolone structure with OH, O, and R¹)

and pharmaceutically acceptable metal complex salts thereof.

2. A pharmaceutical composition for the treatment of humans or non-human animals having a tumor, which comprises an anti-tumor effective amount of the compound according to claim 1, in combination with a pharmaceutically acceptable carrier.

3. A method for the treatment of humans or non-human animals having a tumor, which comprises administering to such human or non-human animal an anti-tumor effective amount of the compound according to claim 1.

* * * * *